US007851458B2

(12) United States Patent
Stone

(10) Patent No.: US 7,851,458 B2
(45) Date of Patent: *Dec. 14, 2010

(54) CARTILAGE ENHANCING FOOD SUPPLEMENTS AND METHODS OF PREPARING THE SAME

(75) Inventor: Kevin R. Stone, Mill Valley, CA (US)

(73) Assignee: Joint Juice, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/189,664

(22) Filed: Jul. 3, 2002

(65) Prior Publication Data

US 2003/0152642 A1 Aug. 14, 2003

Related U.S. Application Data

(63) Continuation-in-part of application No. 09/598,634, filed on Jun. 21, 2000, now Pat. No. 6,432,929, which is a continuation-in-part of application No. 09/338,021, filed on Jun. 22, 1999, now Pat. No. 6,391,864.

(51) Int. Cl.
*A61K 31/7008* (2006.01)
*A61K 31/715* (2006.01)
*A61K 31/726* (2006.01)
*A61K 31/728* (2006.01)
*A61K 31/737* (2006.01)
*A61P 19/02* (2006.01)

(52) U.S. Cl. ............................ 514/62; 514/54; 514/55; 514/557; 514/783; 514/825; 514/974; 424/439; 424/764

(58) Field of Classification Search ................... 424/43, 424/439, 440, 600, 682; 426/72, 74, 520, 426/521, 524, 590, 599, 656, 658; 514/2, 514/23, 53, 54, 783, 904, 905, 62, 55, 825
See application file for complete search history.

(56) References Cited

U.S. PATENT DOCUMENTS

| | | | |
|---|---|---|---|
| 3,679,660 A | 7/1972 | Magnus | 260/211 |
| 3,814,819 A | 6/1974 | Morgan | 426/72 |
| 3,894,148 A | 7/1975 | Ecker | 424/180 |
| 3,901,799 A | 8/1975 | Adkison | 209/144 |
| 4,038,421 A * | 7/1977 | Mendy et al. | 426/72 |
| 4,108,849 A | 8/1978 | Thomas | 260/122 |
| 4,152,462 A | 5/1979 | Hayward et al. | 426/72 |
| 4,309,417 A | 1/1982 | Staples | 424/128 |
| 4,312,856 A | 1/1982 | Korduner et al. | 424/145 |
| 4,322,407 A | 3/1982 | Ko | 424/128 |
| 4,466,958 A | 8/1984 | Morrison | 424/127 |
| 4,543,262 A | 9/1985 | Michnowski | 426/306 |
| 4,647,453 A | 3/1987 | Meisner | 424/54 |
| 4,766,209 A | 8/1988 | Chen et al. | 536/55.3 |
| 5,569,676 A | 10/1996 | Diehl | 514/549 |
| 5,587,363 A | 12/1996 | Henderson | 514/54 |
| 5,629,411 A | 5/1997 | Ishiguro et al. | 536/18.1 |
| 5,795,576 A | 8/1998 | Diaz et al. | 424/195.1 |
| 5,843,919 A | 12/1998 | Burger | 514/62 |
| 5,896,899 A * | 4/1999 | Schmitz | 141/92 |
| 5,922,692 A * | 7/1999 | Marino | 514/54 |
| 6,149,939 A * | 11/2000 | Strumor et al. | 424/464 |
| 6,180,159 B1 * | 1/2001 | Villagran et al. | 426/590 |
| 6,203,827 B1 * | 3/2001 | Katsukura | |
| 6,432,929 B1 * | 8/2002 | Stone | 514/62 |
| 6,482,456 B1 * | 11/2002 | Yokoo et al. | 426/330.3 |
| 6,632,804 B2 * | 10/2003 | Ekanayake | 514/62 |
| 2001/0051134 A1 * | 12/2001 | Pandya | 424/44 |
| 2002/0132780 A1 * | 9/2002 | Heisey et al. | 514/23 |
| 2003/0069202 A1 * | 4/2003 | Kern et al. | 514/46 |
| 2006/0058263 A1 * | 3/2006 | Rogers et al. | 514/62 |
| 2008/0248184 A1 * | 10/2008 | Esteve et al. | 426/597 |

FOREIGN PATENT DOCUMENTS

| | | |
|---|---|---|
| DE | 2103387 | 8/1972 |
| EP | 0 223 540 A2 | 5/1987 |
| EP | 0 587 972 A1 | 3/1994 |
| EP | 0 744 902 B1 | 10/1997 |
| JP | 62224268 | 10/1987 |
| JP | 11-092385 | 4/1999 |
| WO | WO 97/49304 | 12/1997 |

OTHER PUBLICATIONS

Lauscher, "Compositions for the treatment of degenerative joint diseases", Patent No. DE2103387, 1972, abstract.
International Search Report mailed Jan. 31, 2001, International Application No. PCT/US00/40267.
Atkins, Robert C., Dr. Atkins' vita-nutrient solution: nature's answers to drugs, pp. 221-275, 1998.
Dr. H. Siemandi, M.D., et al., The Effect of Cetyl Myristoleate and Adjunctive Therapy on the Course of Arthritic Episodes in Patients with Various Auto-Immune Diseases Characterized by the Common Terminology, Arthritis and "Psoriasis", A Randomized Clinical Trial, Published 1997, Second Quarter.
ACC. 97: 271462 NLDB, Abstract, "Arthred-G Powdered Dietary Supplement—Hydrolyzed," (Jul. 1997).
ACC. 1998: 1404 PROMT, Abstract, "Integris Dietary Supplement—Everlasting Capsules," (Dec. 1997).

* cited by examiner

*Primary Examiner*—John Pak
(74) *Attorney, Agent, or Firm*—Mark G. Lappin

(57) ABSTRACT

A food supplement, either in the form of a snack bar or a beverage, which contains one or more cartilage enhancing supplements is provided. The cartilage supplements include chondroitin, glucosamine, and hyaluronic acid. The food supplement may additionally be fortified with cetyl myristoleate. The beverage is a mixture of a juice drink base which may include a water-based fruit flavored juice prepared using a pasteurization process at a relatively high temperature and a cartilage supplement solution which includes a cartilage supplement prepared at a relatively low temperature. The beverage may be carbonated, non-carbonated or concentrated. The preferred cartilage supplement is glucosamine, preferably associated with a counter ion, more preferably as glucosamine HCl. The supplement also contains vitamin C (ascorbic acid) and calcium hydroxide powder.

20 Claims, No Drawings

CARTILAGE ENHANCING FOOD SUPPLEMENTS AND METHODS OF PREPARING THE SAME

REFERENCE TO RELATED APPLICATIONS

This application is a continuation-in-part of U.S. patent application Ser. No. 09/598,634, filed Jun. 21, 2000, now U.S. Pat. No. 6,432,929, which is a continuation-in-part of U.S. patent application Ser. No. 09/338,021, filed Jun. 22, 1999, now U.S. Pat. No. 6,391,864.

FIELD OF THE INVENTION

The present invention relates to food supplements, such for example, snack bars and beverages that are fortified with one or more cartilage supplements.

BACKGROUND OF THE INVENTION

Nutritional bars and energy drinks are convenient nutritional supplements, particularly for those persons too busy to eat regular meals and for hikers, cyclists, runners or other athletes who need prepackaged, ready-to-eat, high-energy snacks while they are exercising. Such bars and drinks are also convenient nutritional supplements for the elderly who need prepackaged, ready-to-eat snacks. Additionally, such food supplements can supply consumers with the necessary vitamins and minerals specified in the recommended daily allowances provided by the U.S. government.

By way of example, U.S. Pat. No. 4,543,262 discloses a high protein, low or no lactose, vitamin and mineral fortified, nutritionally-balanced snack bar. Additionally, U.S. Pat. No. 3,814,819 teaches a protein-fortified food bar composed of several baked crisp wafers layered on top of the other with a creamy filling between them. The creamy filling contains added vitamins, providing twenty-five percent (25%) of the recommended daily allowance of vitamins and minerals. U.S. Pat. No. 4,152,462 teaches a highly nutritious protein and vitamin enriched food bar, having a marshmallow base. Lastly, U.S. Pat. No. 3,901,799 discloses a high protein chocolate bar. Caseinate and peanut butter are added to a mixture of chocolate and cocoa butter. mixture of chocolate and cocoa butter. Vitamins compatible with the ingredients, it is disclosed, can be added to the snack bar.

Drinks formulations and methods for preparing them have also been developed. Energy enhancement drinks and processes have been developed such as in U.S. Pat. No. 3,894,148, which relates to nutritional and exercise therapy to maximize the storage of glycogen in muscle tissue. Protein fortification drinks have been described in U.S. Pat. No. 4,309,417. Finally, carbohydrate and electrolyte drinks have been described in U.S. Pat. No. 4,312,856 and 4,322,407.

It has been long recognized that dietary cartilage supplements are effective in reducing the symptoms of joint pain. (Drovani, *Clinical Therapeutics*, (1980)). An amino-acid complex combining glutamine with glucosamine sulfate is the constituent component used by the body to make cartilage and connective tissue, which cushion and lubricate the joints in the body. To date, more than 6,000 patients have been studied in 20 clinical trials. These studies have all reached the conclusion that glucosamine sulfate supplements relieve pain and stimulate healing in osteoarthritis patients. In fact, the World Health Organization has officially classified glucosamine sulfate as a slow-acting drug for the treatment of osteoarthritis. Typically, glucosamine sulfate is taken in the form of a pill or a powder.

Chondroitin sulfate is another compound widely sold as an agent for the treatment of the symptoms of joint pain. Its healing properties as a dietary supplement, however, while still effective, have proven in two studies to be lower than the healing properties of glucosamine sulfate. Chondroitin sulfate is also taken in the form of a pill or a powder.

Hyaluronic acid is a polysaccharide that forms a major component of the gel-like substance found in the connective tissue of mammals. Structurally, it is comprised of a repeating disaccharide consisting of N-acetyl-D-glucosamine and D-glucuronic acid. Functionally, it serves as a lubricant and shock absorbent in mammalian joints. Hyaluronic acid is also taken in the form of a pill or a powder and is thought to be effective for the treatment of joint pain.

Cetyl myristoleate (CM) is a newly recognized agent that is potentially useful for the treatment of joint pain. CM is an ester of a fatty acid, the building blocks of fats and oils. CM is produced by combining the fatty acid myristolic acid with cetyl alcohol, a long-chain alcohol. CM appears to function in three ways in the body. First, it shows an anti-inflammatory effect. Second, it appears to act as a lubricant for joints. Third, CM functions as an immune system modulator.

Doctors have reported that significant improvement in patients with osteoarthritis who were taking CM. In 1996, in a one-month multi-center clinical study involving 431 patients with various forms of arthritis, sixty-three percent (63%) of those taking CM showed improvement compared to fourteen percent (14%) in the control group. CM is typically taken orally in the form of an oil.

Konjac flour is a soluble dietary fiber that is similar in structure and function to pectin and typically is used as a thickener, emulsifier, gelling agent, film former and stabilizer. Glucomannan, the main constituent of Konjac flour, is a slightly branched hydrocolloidal polysaccharide having B1-4 linked subunits of glucose and mannose and having a molecular weight ranging between 200,000 and 2,000,000 daltons. Acetyl groups, located every 9-19 subunits along the glucomannan backbone, help solubilize the molecule. In addition to being a food agent, glucomannan has been tested on humans, principally as a means for lowering serum cholesterol, bile acid level and serum triglyceride. Studies indicate that glucomannan may affect glucose tolerance and glucose absorption.

Stevia (*Stevia rebaudiana bectoni*) is a natural, non-caloric sweet-tasting plant that is typically used in medical applications for inhibiting fat absorption and for lowering blood pressure as well as in the food industry as a non-caloric sweetening agent. Stevioside is the component of Stevia that gives the plant its sweetness. As a sugar substitute, it is available as a concentrated liquid, crushed leaf, or concentrated white powder. Often, individuals who do not tolerate sugar or other sweeteners can use Stevia. Medicinally, studies indicate that Stevia helps regulate the pancreas and may help stabilize blood sugar levels within the body. Stevia is also indicated as a cardiotonic, for obesity, to reduce stomach acidity, to reduce gas, for hypotension and to help lower uric acid levels. Research has also indicated that Stevia may help reduce bacteria.

While carbohydrates, proteins and fats are all important in the human diet, carbohydrates are particularly important for athletic performance. Carbohydrates are a well-known source of energy which are readily absorbed by the body. For example, marathon runners and other athletes typically "carbo-load" the day before a race by eating large amounts of carbohydrates. Moreover, athletes in endurance events need a source of energy that is readily absorbable by the body in order to replace the diminishing stores of glucose and glycogen that occur during the event. Lastly, athletes typically consume large quantities of carbohydrates immediately following a race in order to replenish glycogen levels depleted by the event. Thus, the energy source provided by carbohydrates is important to athletes before, during, and after the race.

Typically, carbohydrates range between complex carbohydrates and simple sugars. Structurally, these carbohydrates differ in the number of sugars in the molecule and in the degree of branching. Functionally, they differ by how readily the body can absorb them and process them to derive energy. Thus, the correct ratio of the different types of carbohydrates can supply short-term, mid-term, and long-term supplies of energy to the body.

During athletic events, particularly endurance events such as marathon running, triathalons and long distance cycling, athletes can deplete much, if not all, of their glycogen stores. It is therefore important that athletes replenish their depleted stores of glycogen from a source of carbohydrates. Typically, the cellular machinery used to convert glucose to glycogen is most efficient in the several hours immediately following the athletic event, the so-called recovery period. In addition to depleting their glycogen stores, athletes can cause temporary, and sometimes permanent, damage to the joints of their bodies. Typically, they experience this damage as pain and stiffness in their joints. In some forms, the present invention provides a quality source of carbohydrates, which is important during the recovery period. The invention also provide supplements for the carbohydrate source. In accordance with the invention, the supplements include one or more cartilage supplements which also aid in recovery by reducing joint pain and stiffness, and/or Konjac flour and/or Stevia supplements. The supplements are provided alone or in combination with CM.

It is therefore one object of this invention to provide a formula which provides a nutritional snack together with cartilage supplements which address cartilage dysfunction, and/or a Konjac flour supplement and/or a Stevia supplement.

It is another object of the invention to provide a formula which provides a nutritional snack together with cartilage supplements which address cartilage dysfunction, and/or a Konjac flour supplement and/or a Stevia supplement, in combination with CM.

It is yet another object of this invention to provide a nutritional snack that aids athletes in recovering from athletic events.

Another object of the invention to provide a formula for a beverage including one or more cartilage supplements which address cartilage dysfunction.

It is a further object of the invention to provide a beverage that is source of quality carbohydrates and one or more cartilage supplements.

Yet another object of the invention is to provide a method of preparing a beverage containing one or more cartilage supplements.

SUMMARY OF THE INVENTION

The present invention provides a food supplement, for human and/or animal consumption and methods for making such food supplements. The food supplement can be either in the form of a beverage or a snack bar, or preparation for making such beverages or snack bars. The food supplement of the present invention is fortified with one or more cartilage supplements including glucosamine sulfate, chondroitin sulfate and hyaluronic acid. The food supplements of the invention may also be fortified with Konjac flour and/or Stevia supplements either alone or in combination with the cartilage supplements. The food supplement, as disclosed by the invention, can be optionally further fortified with cetyl myristoleate (CM).

In one preferred embodiment, the present invention provides a high protein, nutritional snack bar that is fortified with one or more cartilage, Konjac flour and/or Stevia supplements, and which can also be fortified with CM. The snack bar has pleasing textural and taste characteristics. In another preferred embodiment, the present invention provides a beverage which is fortified with one or more cartilage, Konjac flour and/or Stevia supplements, and which can be additionally fortified with CM.

All of the compounds used to fortify the food supplement, according to the present invention, are safe for human consumption. Moreover, in addition to the cartilage supplement, any salt, counter ion or derivative of the supplement which is safe for human consumption, and preferably dissociates to the cartilage supplement, either in water or after ingestion, is suitable for use in the present invention. Suitable cartilage supplements are hyaluronic acid, chondroitin, and preferably glucosamine. For chondroitin, sulfate is the preferred counter ion. Where the cartilage supplement is glucosamine, suitable derivatives include but are not limited to, glucosamine n-alkyl sulfonate, and n-acetyl glucosamine. Preferable counter ions for glucosamine include, but are not limited to, phosphoric, sulfate, and, most preferably, hydrochloride. Glucosamine hydrochloride provides improved taste to the nutritional supplements, and thereby minimizes the need for flavorings used to mask the strong flavors characteristic of other cartilage supplements.

In one preferred embodiment, the food supplement containing the cartilage, Konjac flour and/or Stevia supplements, alone or in combination with CM, is a nutritional snack bar. The process of preparing the snack bar, according to the present invention, comprises melting a confectioner's material, which is a solid at ambient temperature. The melted confectioner's material is admixed with the major liquid ingredients and with the major and minor dry ingredients. If the snack bar, according to the present invention, is to be fortified with CM, the CM is first admixed with the major liquid ingredients. Admixing the minor dry compounds with the major liquid ingredients prior to admixing with the confectioner's material minimizes localized concentrations of dry ingredients.

The above mixture is extruded in an extruder typical of extruders known to those skilled in the art. The extruded material or extrudate is then cut to a desired size. The snack bar can be coated on the surface with a melted confectioner's coating material and/or a topping to enhance taste and visual appeal.

In another preferred embodiment, the above-referenced snack bar is modified to include one or more reservoirs, each reservoir containing cartilage, Konjac flour and/or Stevia supplements or mixtures of two or more of such supplements. Within each reservoir, the supplements can be further combined with CM. By way of example, the snack bar can contain a substance such as chocolate or carob, which is molded with one or more internal void regions or reservoirs.

In another preferred embodiment, the cartilage, supplements and/or Konjac flour and/or Stevia supplements and/or the CM are provided in the form of a beverage. Beverages suitable for use in the present invention include naturally or artificially flavored fruit juices, commercially available sports drinks such as GATORADE™ and POWERADE™ beverages, and commercially available nutritionally-balanced beverages such as ENSURE™ beverage.

In a preferred method of making beverages of the invention, a "cold mix" process is used. Pursuant to that process, in a preferred form as noted above, the juice drink base is most preferably a fruit flavored juice. However, the juice drink base could alternatively be unflavored water.

A beverage for human or animal consumption is made from a mixture of a juice drink base and a cartilage supplement-containing solution. The juice drink base is a water-based solution, and is preferably a flavored (and most preferably a naturally or artificially fruit-flavored) juice. In one embodiment, the juice drink base is prepared using a pasteurization process at a relatively high temperature. The high temperature is naturally or artificially sufficient to kill bacteria. The cartilage supplement-containing solution is a water-based solution containing one or more cartilage supplements (such as glucosamine, chondroitin, hyaluronic acid, or mixtures thereof) prepared at a relatively low temperature. Preferably, the low temperature is in a range that minimizes inactivation of the cartilage supplement. The beverage may be carbonated or non-carbonated; furthermore, the beverage can be in a concentrated form for later dilution by the consumer or ready to drink.

In yet another embodiment of the invention there is provided a method of treating cartilage dysfunction in a human by administering a cartilage enhancing beverage formulated according to the above aspects of invention.

In still another embodiment of the invention there is provided a food supplement fortified with one or more of the cartilage supplements described herein, and further including vitamin C (ascorbic acid) and calcium hydroxide powder as components.

DETAILED DESCRIPTION OF THE PREFERRED EMBODIMENTS

The food supplement, snack bar and beverage of the invention advantageously contains several components that promote healthy joints by providing supplemental nutrition used by the body in making the components of healthy joints. In other words, the invention provides supplements the body's natural metabolism to promote healthy collagen, cartilage and bone.

Vitamin C is an important anti-oxidant; it is essential for making the integrity of collagen proteins involved in the building and health of cartilage and joints. Collagen protein requires vitamin C for "hydroxylation," a process that allows the molecule to achieve the best configuration and prevents collagen from becoming weak and susceptible to damage. Beyond that, recent evidence indicates that vitamin C increases the level of procollagen messenger RNA. Collagen subunits are formed within fibroblasts as procollagen, which is excreted into extracellular spaces. Vitamin C is required to export the procollagen molecules out of the cell. Gaby S K & Singh V N, In *Vitamin Intake and Health: A Scientific Review*, S. K. Gaby, A. Bendich, V. Singh and L. Machlin (eds.), pp. 103-1043 (Marcel Dekker, N.Y. 1991).

Calcium generally provides comprehensive nutritional support for the bones and cartilage in joints and other skeletal structure elements. Cartilage is composed of fibrous collagen in an amorphous gel.

It is known that joint cartilage can become damaged due to a sudden trauma (auto accident), or over an extended period of time (sports). A deficiency in minerals, such as calcium, can lead to improper cartilage formation following such a trauma. A nutritional deficiency of the molecules that make up cartilage can also lead to the formation of arthritis.

Moreover, it is also known that prolonged deficiency of calcium produces generalized bone demineralization and porosis, and thus weak joints. The organic (nonmineral) content of bone is made up largely of collagen fibers with calcium salt crystals lying adjacent to each segment of the fiber.

In summary, the invention, with the components of cartilage supplements (such as hondroitin, glucosamine, and hyaluronic acid), vitamin C, and calcium hydroxide are useful for and, in combination, advantageously provide a nutritional supplement for healthy joints.

Commercially available confectioner's coating material is used in the present invention. The compositions of typical confectioner's coating materials which can be used in the present invention, are disclosed in cookie and cracker technology, *AVI Publishing Co.*, Westport, Conn., page 176, table 45 (1968). These materials are generally solid at room temperature, but melt and can be poured when heated. The confectioner's material in the present invention preferably has melting points below 140° F. and more preferably below 105° F.

Confectioner's material with higher melting or pouring points can present several difficulties. For example, the higher the melting point of the coating material, the greater is the risk that the heated coating material will begin to set or partially solidify when admixed with the other ingredients that are preferably maintained at room temperature. Premature hardening of the coating material can cause a lack of uniform distribution of the confectioner's material within the snack bar. As a result, any ingredients added to the confectioner's material may also not be uniformly distributed throughout the product. This is particularly true of flavoring ingredients that may be added to the melted confectioner's material.

In the present invention, the confectioner's coating material may be cocoa butter-based or alternatively may be a compound coating, which is made from hardened vegetable oils. Examples of hardened vegetable oils used for compound coatings include cottonseed, coconut, soybean, palm and peanut oils. These hardened vegetable oils are mixed with sugar and are the principle ingredients in the coating material. Compound coatings may be peanut flavored, fruit flavored, chocolate flavored, vanilla flavored, coconut flavored or flavored with other commercially available flavorings.

The snack bar according to the present invention, can be fortified with protein from several sources of edible protein, either alone or in combination. Exemplary sources include whey powder, carob powder, soy lecithin, peanut flour, wheat proteins such as wheat germ and caseinates such as calcium, potassium and sodium caseinates.

Exemplary sources of carbohydrates suitable for the snack bar of the present invention include malted cereal syrup from corn, barley and brown rice; maltodextran; fructose; high fructose corn syrup; date paste; sucrose; brown sugar and mixtures thereof. Exemplary sources of complex carbohydrates include those derived from cereal grains such as oats, rice, barley, and corn. Preferably, the snack bar according to the present invention, contains at least one sugar and at least one cereal grain as the sources of carbohydrates.

In the present invention, corn syrup, preferably high fructose corn syrup, is used as a source of carbohydrates. The corn syrup gives the snack a moist chewy texture, provides a source of sweetness to the snack bar, and aids in distributing the dry ingredients. Additionally, the corn syrup together with the confectioner's coating material, binds together the other ingredients such as the protein source ingredients and the cereal grain ingredients.

Fats have the highest source of energy per unit weight, approximately twice that of proteins or carbohydrates. In addition to the confectioner's coating material, other sources of fat suitable for use in the present invention include flavoring such as chocolate, cocoa, and coconut and at least one partially hydrogenated vegetable oil such as soybean, cottonseed, corn and palm oil.

The above-listed ingredients are categorized based on the main nutritional component that each contributes to the snack bar. It is, however, useful to note that many of the ingredients may be sources of two or more nutritional components. For example, whey powder, peanut flour, and wheat germ each contain substantial amounts of carbohydrates, proteins, and fats. By varying the ingredients in the snack bar, one can maintain the caloric distribution disclosed by the present invention.

Several additional ingredients are preferably added to the snack bar according to the present invention. For example, the snack bar may be topped with conventional toppings such as crushed nuts, granola and the alike. Additionally, although shortenings other than the confectioner's coating are not necessary, it is preferable to include a wetting agent to facilitate mixing and binding of the dry ingredients with the confectioner's coating and corn syrup and to enhance the moisture and chew capability of the snack. Suitable wetting agents for use in the present invention include molasses, honey, and the partially hydrogenated vegetable oils.

The nutritional snacks according to the present invention, are made by first melting the confectioner's coating material by heating it to its melting point or to within about ten degrees (10°) Fahrenheit above its melting point. Next, the liquid ingredients that comprise the corn syrup, the melted confectioner's coating material, and the optional wetting agent are mixed together. If the snack bar is to be fortified with cetyl myristoleate (CM), the CM is added to the liquid ingredients. The liquid ingredients are mixed to substantial homogeneity.

Once the liquid ingredients are thoroughly mixed, the minor dry ingredient are mixed into the liquid ingredients. The minor dry ingredients include the chondroitin sulfate, the glucosamine sulfate, the hyaluronic acid and the optional salt. The minor dry ingredients are mixed with the liquids in order to avoid localized high concentrations of the minor dry ingredients.

Once the minor dry ingredients are mixed to substantial homogeneity with the liquid ingredients, the major dry ingredients are then admixed to the liquid ingredients and the minor dry ingredients. This mixture is mixed to substantial homogeneity. Major dry ingredients include the high content carbohydrates such as sugars and cereal grains and the high content proteins such as the whey protein, soy protein, peanut protein and caseinate.

Flavoring ingredients such as cocoa or coconut can be added to the mixture. When adding flavoring ingredients, it is preferable to add them to the liquid ingredients to avoid localized concentrations within the snack bar. Once all the ingredients are mixed to substantial homogeneity, the mixture is transferred to a conventional confectionery-type bar extruder. The mixture is forced through a die of the extruder to form the extrudate. The die may be any shape known to those skilled in the art, but is preferably rectangular. The extrusion is done at room temperature.

After extrusion, the extrudate is cut to the desired size. The cut extrudate may then be coated by, for example, dipping with a melted confectioner's coating material. The bar is then chilled and may then be topped with a topping such as granola or ground nuts. The bar is then packaged for shipping or storage.

In another preferred embodiment, the cartilage supplements, either alone or in combination with the CM, are supplied in the form of a beverage. By way of non-limiting example, beverages suitable for use in the present invention include water or fruit juices such as apple juice, orange juice, grapefruit juice, cranberry juice, pineapple juice, grape juice, and mixtures thereof. Other beverages suitable for use in the present invention include commercially available sports drinks such as GATORADE™ and POWERADE™ beverages. Generally, these sports drinks provide calories substantially only in the form of carbohydrates and provide electrolyte replacements, which are thought to aid in recovery after exercise. Lastly, commercially available nutritionally balanced beverages, such for example ENSURE™ beverage, are suitable for use in the present invention. These nutritionally balanced beverages generally provide carbohydrates, protein, fat, vitamins and minerals to consumers and often serve as meal replacements.

In accordance with the invention, all three cartilage supplements, either alone or in combination, are included in beverages, such as the above-identified beverages. Where CM is included, it is important to note, however, that CM is an oily-like substance and, therefore, tends not to be readily miscible with the aqueous based beverages. Accordingly, when CM is added to a beverage according to the present invention, it is first emulsified. Emulsifying agents and methods known to those skilled in the art are suitable for use in the present invention. The emulsifying agent chosen is fit for human consumption. Suitable emulsifying agents include gum arabic and gelatin. The emulsions are prepared by shaking together the two liquids or by adding one phase drop-wise to the other with some form of agitation, such as irradiation by high intensity ultrasonic waves.

In a preferred method, the cartilage enhanced beverages made according to the present invention are made using a multi-step process. As a first step, a juice drink base is prepared. Water, flavorings, and preservatives are mixed together in predetermined amounts. The solution is heat pasteurized, and cooled to ambient temperatures. The juice base may be prepared and stored for later use, or used immediately in the production of the final beverage products.

As a second step, a second solution of "cartilage supplement solution", containing the cartilage supplement, and, if and as desired, additional flavorings and carbohydrates, is prepared at temperatures below those used in a heat pasteurization process, preferably but not necessarily, at ambient temperatures or lower. As a third step, the drink base is combined with the cartilage supplement solution at ambient temperatures. The combined solution is adjusted for acidity, and preferably, but not necessarily, chilled to temperatures below ambient and above freezing, and carbonated. The multi-step method insures that the cartilage supplement is not affected by the preparation and/or bottling process. As an alternative, the second and third steps may be combined, where the ingredients for the cartilage supplement solution are added directly to the juice drink base, and pH adjusted, and if desired, carbonated. That combined second and third step is performed, preferably but not necessarily, at temperatures below those used in a heat pasteurization process.

In another embodiment, a beverage concentrate is prepared. Juice base, sweetener, water, preservatives and, optionally, vitamins, and/or minerals, are mixed in a mixing tank and pasteurized. The resulting product is transferred from the mixing tank to the packaging through transfer lines. The product cools in the transfer lines as it flows from the mixing tank to the packaging. The product temperature is lowered by radiational cooling of the product flowing through the transfer lines, or optionally, the lines may be chilled.

Preferably, the cartilage supplement solution is introduced into the liquid stream at a point in transfer lines, preferably at a distance from the mixing tank, where the temperature of the flowing liquid is lower than the temperature in the mixing tank. This allows the cartilage solution to mix into the product at temperatures below pasteurization temperature and as the beverage solution is cooling continuously in transit. Once in the packaging, the containers are sealed, and sprayed or doused with cool water to lower the temperature of the final product to approximately ambient temperature.

In this embodiment, the total residence time of the cartilage solution at elevated temperatures is minimal, thereby minimizing any heat inactivation of the cartilage supplement. For example, the product temperature may be close to 195° F. at the mix tank. As the fluid progresses through the transfer lines, the point where the glucosamine is added may be 150° F. or less. As the solution passes to the packaging it is continually cooled so that at the point of packaging, the solution temperature at the packaging point may be approximately 100° F. to 80° F. After packaging, the final product is cooled to ambient temperature. Thus, in this example, the total residence time of glucosamine near pasteurization temperatures may be only about 30 seconds while undergoing continuous cooling.

The heat pasteurization process for the juice base is dependent on both the temperature employed and the residence time of the solution at that temperature. Generally, and within a range, the lower the temperature used, the longer the solution should be processed to insure adequate microbial control. Pasteurization parameters can range from a low of about 165° F. for 3 minutes to about 200° F. for less than 40 seconds, The preferable parameters are 195±4° F. for 42±4 seconds.

The beverage of the present invention is also prepared by:
(A) providing a juice drink base, said juice drink base being a solution of water, ascorbic acid, potassium sorbate and naturally or artificially flavored fruit juice, prepared using a heat pasteurization process at a temperature above 190° F.,
(B) providing a cartilage supplement-containing solution, which is a water-based solution comprising one or more cartilage supplements and prepared at a temperature of 150° F. or below, whereby inactivation of the cartilage supplement is substantially minimized, and wherein said one or more cartilage supplements are selected from the group consisting of glucosamine, glucosamine salts, glucosamine associated with a counterion, glucosamine derivatives that dissociate to glucosamine in water or after ingestion, chondroitin, chondroitin salts, chondroitin associated with a counterion, and hyaluronic acid,
(C) forming a mixture by cooling the juice drink base to a temperature of 150° F. or less, and adding and mixing the cartilage supplement-containing solution and a sweetener, wherein the sweetener is stevia, and
(E) adjusting the pH of the mixture in the range of 2.2 to 4.6 to obtain the beverage.

In an alternate embodiment, the cartilage supplement may be added directly to the juice base and other ingredients at or near pasteurization temperatures. In yet another embodiment, the cartilage supplement may be added to the mix tank with the juice base and other ingredients, and the product may be pasteurized using pasteurization processes that do not include heat processing, such as, but not limited to, filter sterilization or radiation sterilization.

The juice bases, pre-carbonated product, and concentrated beverage solutions are measured for Brix (a measure of soluble solids), and titratable aciditiy (TA) and adjusted as necessary, using water and citric acid, respectively. The pre-carbonated ready to drink product and concentrated beverage product are also pH adjusted just before carbonation and packaging, respectively.

The beverages produced by these various embodiment include, but are not limited to ready to drink carbonated beverages, ready to drink non-carbonated beverages, and concentrated beverage mixes, i.e., mixes that are diluted to drinking concentration (with water, juice, carbonated water, and the like) by the consumer.

EXAMPLE 1

In this example, a snack bar with a surface coating is prepared. The ingredients and relative amounts are shown in Table 1.

The snack bar of the present invention is made by melting the confectioner's peanut butter material and mixing in a conventional mixer, the liquid components that comprise the high fructose corn syrup and the molasses.

The second step is to add the minor dry ingredients comprising the salt, chondroitin sulfate, glucosamine sulfate and the hyaluronic acid, to the liquid mixture. The mixture is mixed to substantial homogeneity.

The third step in the process is adding the major dry ingredients to the mixed ingredients of the second process step. The major dry ingredients include the sugars, whey protein, rice flour and soy protein. The mixture is then mixed to substantial homogeneity. The mixture is then fed into a conventional extruding machine.

The mixture is extruded at room temperature. As the mixture is extruded, the extrudate is cut into individual serving sizes of about sixty (60) grams. The cut pieces are then coated with approximately ten (10) grams of melted chocolate confectioner's material. The bar is then allowed to cool or is chilled and is wrapped for shipping and storage. The final bar is approximately seventy (70) grams and has bout three hundred (300) calories.

EXAMPLE 2

A nutritional bar with a core, a surface coating and a topping is prepared. The bar is further fortified with CM. The ingredients and relative amounts are shown in Table 2.

The snack bar is made by melting chocolate confectioner's coating material. The corn syrup, vegetable oil and CM are next added to the melted confectioner's coating.

Next, the minor dry ingredients, as set forth in Example 1, are mixed with the liquids, along with the flavorings. The mixture is mixed to substantial homogeneity.

To this mixture, the major dry ingredients are then added. These include the bran, oats, barley, fructose, caseinate, and the wheat germ. The mixture is then mixed to substantial homogeneity.

The mixture is then processed as set forth in Example 1. The bar is then coated with approximately ten (10) grams of melted chocolate confectioner's coating and then topped with crushed nuts. The bar is then packaged for shipping and storage.

EXAMPLE 3

The beverage of the present invention containing cartilage supplements is produced as follows:

First, a volume of GATORADE is aliquoted into a conventional fluid mixer. Hyaluronic acid and/or, glucosamine sulfate, and/or chondroitin sulfate are next added to the solution to a final concentration of four percent (4%) (weight to volume) of each component. The solution is next mixed until the added ingredients become solubilized. The solution is then aseptically filled into individual serving size bottles of approximately five hundred milliliters (500 ml).

EXAMPLE 4

The beverage of the present invention containing a cartilage supplement and CM is produced as follows:

First, CM is emulsified with any known emulsifying agent suitable for human consumption. Next, a volume of ENSURE is aliquoted into a conventional fluid mixer. The emulsified CM is added to a final concentration of two percent (2%) (volume to volume). Next, the hyaluronic acid, glucosamine sulfate, and chondroitin sulfate are added to the solution to a final concentration of four percent (4%) (weight to volume). The solution is mixed until the added cartilage supplements become solubilized. The solution is then aseptically filled into individual serving size bottles of approximately five hundred milliliters (500 ml).

EXAMPLES 5-7

Preparation of the Juice Drink Base.

Juice drink base solutions containing the ingredients and proportions shown in Table 3 were prepared and stored for later use formulating the finished beverage products.

For each flavor, the above ingredients were mixed together using 90% of the water. The Brix, titratable acidity and pH were adjusted, using the remaining 10% of the water. The resultant solution was pasteurized by heating the solution to 195° F. and maintaining it at that temperature for approximately 40 seconds. Then the solution was cooled to ambient temperature to complete preparation of the drink base. In these examples of the juice drink base, the Brix, and titratable acidity values were adjusted to the ranges shown in Table 4. These values may vary by about ±5 percent. The juice base was then stored for later use in formulating the final products.

EXAMPLES 8-10

Preparation of Ready to Drink Beverages:

Ready to drink cartilage enhancing supplement-enhancing beverages were prepared at ambient temperature using the ingredients (and proportions) shown in Table 5.

Initially, sodium benzoate was added to 50% of the total water, and mixed at ambient temperature until the sodium benzoate was dissolved. That solution was maintained under continuous agitation. The glucosamine HCl, citric acid, Juice Drink Base and high fructose corn syrup were each added separately to the solution and mixed thoroughly. Ninety percent (90%) of the remaining water was then added and the solution was mixed for 15 minutes. The Brix, titratable acidity and pH were adjusted using the remaining water, and if necessary, using additional citric acid. The resulting solution was then carbonated in a proportioner (1+4) at 40° F. to 3.0 volumes. The resulting beverage was then ready for bottling.

The acceptable ranges for Brix, and TA in the beverages before and after carbonation, and pH after carbonation are shown in Table 6:

EXAMPLES 11-13

Preparation of Sugar Free Ready to Drink Beverages:

Sugar free (diet) ready to drink cartilage enhancing supplement-enhancing beverages were prepared at ambient temperature using the ingredients (and proportions) shown in Table 7.

Initially, sodium benzoate was added to 50% of the total water, and mixed at ambient temperature until the sodium benzoate was dissolved. That solution was maintained under continuous agitation. The glucosamine HCl, citric acid, aspartame, acesulfame K, and Juice Base were each added separately to the solution and mixed thoroughly. Ninety percent (90%) of the remaining water was then added and the solution was mixed for 15 minutes. The Brix, titratable acidity and pH were adjusted using the remaining water, and if necessary, using additional citric acid. The resulting solution was then carbonated in a proportioner (1+4), to 3.0 volumes, and further adjusting the pH. The resulting beverage was then ready for bottling.

Brix, TA, and pH of the beverages before and after carbonation are measured. Table 8 shows the acceptable ranges after carbonation.

EXAMPLES 14-17

Preparation of Concentrated Juice Bases.

Concentrated cartilage enhancing supplement beverages were prepared using the ingredients (and proportions) shown in Table 9.

Preparation of Concentrated Beverage:

Initially, 50% of the water was pumped into the mixing tank. Sodium benzoate was added to the water and thoroughly mixed. Citric acid, sweetener (high fructose corn syrup or artificial sweeteners) and Juice Base were added to the solution and thoroughly mixed. Brix and TA were adjusted using a measured amount of the remaining water and citric acid, respectively. The concentrated juice bases were heat pasteurized at approximately 195° F. for about 42 seconds.

The solution was pumped through transfer lines to the packaging area. Glucosamine HCl (dissolved in a measured amount of water) was fed into the fluid stream in the transfer lines. Brix, TA and pH were tested on the finished product, and the batch parameters were adjusted appropriately, as shown in Table 10. The packages were sealed, and rinsed with water at ambient temperature. Yield: approximately 7,060 two ounce packages, depending on flavor.

TABLE 1

Snack Bar Formulation

| Ingredients | Total Weight (%) |
| --- | --- |
| Whey Protein | 24.5 |
| Sugars | 8.0 |
| Rice Flour | 16.0 |
| Soy Protein | 6.0 |
| Chondroitin Sulfate | 1.5 |
| Glucosamine Sulfate | 1.5 |
| Hyaluronic Acid | 1.5 |
| Salt | 0.5 |
| Corn Syrup | 28.5 |
| Molasses | 4.0 |
| Confectioner's Peanut Butter | 8.0 |
| TOTAL | 100.0 |

TABLE 2

Nutritional Bar with Topping

| Ingredients | Weight Percentage |
| --- | --- |
| Bran | 2.5 |
| Oat | 10.0 |
| Barley | 4.0 |
| Fructose | 6.0 |
| Caseinate | 11.0 |
| Flavorings | 4.0 |
| Wheat Germ | 13.0 |
| Chondroitin Sulfate | 1.5 |
| Glucosamine Sulfate | 1.5 |
| Hyaluronic Acid | 1.5 |
| Salt | 0.5 |
| Corn Syrup | 25.0 |
| Partially Hydrogenated Vegetable Oil | 1.0 |
| Cetyl Myristoleate (CM) | 1.5 |
| Chocolate Confectioner's Compound Coating | 18.5 |
| TOTAL | 100.0 |

TABLE 3

Juice Base Formulations

| Ingredients | Example 5 Orange Wt % | lb. | Example 6 Lemon Wt. % | lb. | Example 7 Tropical Wt % | lb. |
|---|---|---|---|---|---|---|
| Water | 20.6419 | 47.30 | 2.93 | 6.72 | 16.7984 | 41.69 |
| Ascorbic Acid | 0.8505 | 1.95 | 1.75 | 4.00 | 0.8500 | 2.11 |
| Natural Juicy Citrus Accord | 1.2430 | 2.85 | 2.55 | 5.84 | 2.0922 | 5.19 |
| Sodium Benzoate | 0.1000 | 0.23 | 0.10 | 0.23 | 0.1000 | 0.25 |
| Potassium Sorbate | 0.1000 | 0.23 | 0.10 | 0.23 | 0.1000 | 0.25 |
| Orange Juice Concentrate | 65.0274 | 149.01 | — | — | 55.8683 | 138.64 |
| Natural Tangerine Flavor | 7.3270 | 16.79 | — | — | 2.6153 | 6.49 |
| Natural Orange Flavor Powder | 2.6168 | 6.00 | — | — | 2.0922 | 5.19 |
| Natural Orange Flavor Emulsion | 2.0934 | 4.80 | — | — | — | — |
| Lemon Juice Concentrate | — | — | 69.95 | 160.18 | — | — |
| Natural Lemon Flavor, WONF | — | — | 19.40 | 44.43 | — | — |
| Natural Lemon Extract Flavor | — | — | 3.22 | 7.38 | — | — |
| Mango Concentrate | — | — | — | — | 12.1609 | 30.18 |
| Natural Mango Flavor | — | — | — | — | 0.9480 | 2.35 |
| Passionfruit Concentrate | — | — | — | — | 5.2305 | 12.98 |
| Natural Red Color, liquid | — | — | — | — | 1.1442 | 2.84 |
| TOTAL (gallons) | 100.00 | 229.16 (25) | 100.00 | 229.01 (24) | 100.00 | 248.16 (25) |

TABLE 4

Brix, and TA* values for Juice Base

|  | Orange | Lemon | Tropical |
|---|---|---|---|
| Brix | 42.6 | 33.3 | 42.7 |
| TA | 3.13 | 29.72 | 3.63 |

TA* = titratable acidity; acceptable ranges are within ±5%.

TABLE 5

Ready to Drink Beverages

| Ingredients | Example 8 Orange Wt % | lb. | Example 9 Lemon Wt. % | lb. | Example 10 Tropical Wt % | lb. |
|---|---|---|---|---|---|---|
| Water | 39.81 | 591.40 | 62.45 | 872.16 | 39.63 | 589.43 |
| High Fructose Corn Syrup | 42.02 | 624.24 | 28.39 | 396.43 | 41.96 | 624.32 |
| Glucosamine HCl | 2.38 | 35.36 | 2.41 | 33.69 | 2.38 | 35.37 |
| Citric Acid | 2.21 | 32.90 | 0.00 | 0.00 | 2.46 | 36.60 |
| Sodium Benzoate | 0.23 | 3.37 | 0.24 | 3.31 | 0.23 | 3.37 |
| Tangerine Orange Base (Example 5) | 13.35 | 198.38 | — | — | — | — |
| Lemon Juice Base (Example 6) | — | — | 6.51 | 91.22 | — | — |
| Tropical Juice Base (Example 7) | — | — | — | — | 13.34 | 198.52 |
| TOTAL (gallons) | 100.00 | 1485.65 (150) | 100.00 | 1396.81 (150) | 100.00 | 1487.61 (150) |

TABLE 6

Brix, TA* and pH Acceptable Ranges Before and After Carbonation

|  | Orange | | Lemon | | Tropical | |
|---|---|---|---|---|---|---|
|  | Before Carb. | After Carb. | Before Carb. | After Carb. | Before Carb. | After Carb. |
| Brix | 43.1° ± 5% | 9.2-10.4° | 27.0° ± 5% | 7.0-8.6° | 43.3° ± 5% | 9.2-10.4 |
| TA | 2.62 ± 5% | 0.53-0.58 | 1.95 ± 5% | 0.55-0.57 | 3.63 ± 5% | 0.55-0.66 |
| pH | — | 3.48-3.56 | — | 3.49-3.56 | — | 3.34-3.55 |

*TA = titratable acidity

TABLE 7

Sugar Free Ready to Drink Beverages

|  | Example 11 Orange Diet | | Example 12 Lemon Diet | | Example 13 Tropical Diet | |
|---|---|---|---|---|---|---|
| Ingredients | Wt % | lb. | Wt. % | lb. | Wt % | lb. |
| Water | 81.795 | 1215.64 | 89.981 | 1256.91 | 81.560 | 1213.74 |
| Aspartame | 0.025 | 0.37 | 0.267 | 0.37 | 0.025 | 0.37 |
| Glucosamine HCl | 2.380 | 35.36 | 2.407 | 33.63 | 2.377 | 35.37 |
| Citric Acid | 2.214 | 32.90 | 0.805 | 11.25 | 2.460 | 36.60 |
| Sodium Benzoate | 0.227 | 3.37 | 0.237 | 3.31 | 0.226 | 3.37 |
| Acesulfame K | 0.012 | 0.18 | 0.013 | 0.18 | 0.012 | 0.18 |
| Tangerine Orange Base (Example 5) | 13.347 | 198.38 | — | — | — | — |
| Lemon Juice Base (Example 6) | — | — | 6.530 | 91.22 | — | — |
| Tropical Juice Base (Example 7) | — | — | — | — | 13.340 | 198.52 |
| TOTAL (gallons) | 100.00 | 1486.20 | 100.00 | 1396.87 | 100.00 | 1488.15 |
|  |  | (150) |  | (150) |  | (150) |

TABLE 8

Target Values and Ranges for pH, Brix and TA* for Sugar Free Beverages

|  | Diet Orange After Carbonation | Diet Lemon After Carbonation | Diet Tropical After Carbonation |
|---|---|---|---|
| Brix Range | 2-4° | 2-4° | 2-4° |
| TA Range | 0.68-0.73 | 0.65-0.70 | 0.82-0.87 |
| pH Range | 2.75-2.95 | 2.70-2.90 | 2.80-2.95 |

TA* = titratable acidity

TABLE 9

Concentrated Juice Beverages

|  | Example 14 Orange | | Example 15 Lemon | | Example 16 Diet Lemon | | Example 17 Tropical | |
|---|---|---|---|---|---|---|---|---|
| Ingredients | Wt % | lb. | Wt. % | lb. | Wt. % | lb. | Wt % | lb. |
| Water | 17.401 | 188.24 | 47.978 | 511.34 | 86.430 | 921.22 | 17.106 | 185.59 |
| High Fructose Corn Syrup | 57.736 | 624.58 | 38.504 | 410.37 | — | — | 57.735 | 626.40 |
| Glucosamine HCl | 3.158 | 34.16 | 3.157 | 33.65 | 3.157 | 33.65 | 3.158 | 34.26 |
| Citric Acid | 3.052 | 33.01 | 1.093 | 11.65 | 1.094 | 11.66 | 3.387 | 36.74 |
| Sodium Benzoate | 0.317 | 3.43 | 0.326 | 3.48 | 0.326 | 3.48 | 0.317 | 3.44 |
| Aspartame | — | — | — | — | 0.035 | 0.38 | — | — |
| Acesulfame K | — | — | — | — | 0.018 | 0.19 | — | — |
| Tangerine Orange Base (Example 5) | 18.336 | 198.38 | — | — | — | — | — | — |

TABLE 9-continued

Concentrated Juice Beverages

| | Example 14 Orange | | Example 15 Lemon | | Example 16 Diet Lemon | | Example 17 Tropical | |
|---|---|---|---|---|---|---|---|---|
| Ingredients | Wt % | lb. | Wt. % | lb. | Wt. % | lb. | Wt % | lb. |
| Lemon Juice Base (Example 6) | — | — | 8.942 | 95.29 | 8.940 | 95.29 | — | — |
| Tropical Juice | — | — | — | — | — | — | 18.297 | 198.52 |
| Base (Example 7) | | | | | | | | |
| TOTAL | 100.00 | 1081.80 | 100.00 | 1065.78 | 100.00 | 1065.87 | 100.00 | 1084.94 |

TABLE 10

Acceptable Ranges for pH, Brix and TA* for Concentrate Beverages

| | Orange | Diet Lemon | Lemon | Tropical |
|---|---|---|---|---|
| Brix | 55-59° | 7-11° | 35-39° | 55-59° |
| TA | 4.10-4.17 | 3.85-3.93 | 3.75-3.83 | 4.55-4.60 |
| pH | 2.25-2.40 | 2.25-2.35 | 2.30-2.45 | 2.20-2.35 |

TA* = titratable acidity

EXAMPLES 18

Beverages Containing Cartilage Supplements, Vitamin C and Calcium Salt

The following Tables provide examples of various beverages and food supplements, each fortified with one or more cartilage supplements including glucosamine sulfate, chondroitin sulfate and hyaluronic acid, and further including vitamin C (ascorbic acid) and calcium salt (such as calcium hydroxide powder) as components.

TABLE 11

11.6 oz. Lemon RTD Beverage - w/10% Calcium & 100% Vitamin C & glucosamine HCl

| Ingredient | Supplier | Code | Weight (g) | Percent |
|---|---|---|---|---|
| Water | | | 300.18 | 91.279% |
| 55 HFCS | Cargill | 55% | 21.09 | 6.413% |
| Lemon Juice Concentrate | Vita-Pakt | 244 | 3.43 | 1.043% |
| Glucosamine HCl | Biosynergy | | 1.79 | 0.544% |
| Natural Lemon Flavor, WONF | Givaudan Roure | 881937 | 0.95 | 0.289% |
| Citric Acid | ADM | fine granular | 0.60 | 0.182% |
| Calcium Hydroxide Powder | VWR Scientific | 1374-01 | 0.26 | 0.079% |
| Sodium Benzoate Powder, F.C.C. | Spectrum Chemical | S1146 | 0.18 | 0.055% |
| Natural Lemon Extract Flavor | Ungerer | FG8949 | 0.16 | 0.049% |
| Natural Juicy (Citrus) Accord | Robertet | NV-18, 216 | 0.13 | 0.040% |
| Ascorbic Acid Powder, F.C.C. | Spectrum Chemical | A1371 | 0.08 | 0.024% |
| Potassium Sorbate Powder, F.C.C. | Spectrum Chemical | P1408 | 0.01 | 0.003% |
| | | | 328.86 | 100.000% |

YIELD: 100%

Procedure for making 11.6 oz. Lemon RTD Beverage—w/10% Calcium & 100% Vitamin C & glucosamine HCl:
1. Dissolve sodium benzoate and potassium sorbate in water.
2. Preblend all other dry ingredients.
3. Add preblend to water with sodium benzoate & potassium sorbate.
4. Stir until completely dissolved.
5. Add all remaining ingredients.
6. Mix together well.
7. Carbonate.

Specifications for 11.6 oz. Lemon RTD Beverage—w/10% Calcium & 100% Vitamin C & glucosamine HCl:
pH: 3.49
Brix: 7°
TA: 0.557

TABLE 12

11.6 oz. Tangerine Orange Joint Juice - w/10% Calcium, 100% Vitamin C, 1500 mg Glucosamine HCl

| Ingredient | Supplier | Code | Weight (g) | Percent |
|---|---|---|---|---|
| Water | | | 285.35 | 86.769% |
| 55 HFCS | Cargill | 55% | 31.64 | 9.621% |
| Orange Juice Concentrate | Vita-Pakt | 185 | 6.54 | 1.989% |
| Glucosamine HCl | Biosynergy | | 1.79 | 0.544% |
| Citric Acid | ADM | fine granular | 1.67 | 0.508% |
| Natural Mandarin Orange Flavor | Givaudan-Roure | 470603 | 0.74 | 0.225% |
| Calcium Hydroxide Powder | VWR Scientific | 1374-01 | 0.26 | 0.079% |
| Natural Orange Flavor | Robertet | NV-6507 | 0.26 | 0.079% |
| Natural Orange Flavor Emulsion | Edlong Corporation | 460 | 0.21 | 0.064% |
| Sodium Benzoate Powder, F.C.C. | Spectrum Chemical | S1146 | 0.18 | 0.055% |
| Natural Juicy (Citrus) Accord | Robertet | NV-18, 216 | 0.13 | 0.040% |
| Ascorbic Acid Powder F.C.C. | Spectrum Chemical | A1371 | 0.08 | 0.024% |
| Potassium Sorbate Powder, F.C.C. | Spectrum Chemical | P1408 | 0.01 | 0.003% |
| | | | 328.86 | 100.00% |

YIELD: 100%

Procedure for making 11.6 oz. Tangerine Orange Joint Juice—w/10% Calcium, 100% Vitamin C, 1500 mg Glucosamine HCl:

1. Dissolve sodium benzoate and potassium sorbate in water.
2. Preblend all other dry ingredients.
3. Add preblend to water with sodium benzoate & potassium sorbate.
4. Stir until completely dissolved.
5. Add all remaining ingredients.
6. Mix together well.
7. Carbonate.

Specifications for 11.6 oz. Tangerine Orange Joint Juice—w/10% Calcium, 100% Vitamin C, 1500 mg Glucosamine HCl:

pH: 3.48

Brix: 10.4°

TA: 0.58

TABLE 13

11.6 oz. Tangerine Orange Joint Juice - w/10% Calcium, 100% Vitamin C, 1500 mg Glucosamine HCl

| Ingredient | Supplier | Code | Weight (g) | Percent |
|---|---|---|---|---|
| Water | | | 285.35 | 86.769% |
| 55 HFCS | Cargill | 55% | 31.64 | 9.621% |
| Orange Juice Concentrate | Vita-Pakt | 185 | 6.54 | 1.989% |
| Glucosamine HCl | Biosynergy | | 1.79 | 0.544% |
| Citric Acid | ADM | fine granular | 1.67 | 0.508% |
| Natural Mandarin Orange Flavor | Givaudan-Roure | 470603 | 0.74 | 0.225% |
| Calcium Hydroxide Powder | VWR Scientific | 1374-01 | 0.26 | 0.079% |
| Natural Orange Flavor | Robertet | NV-6507 | 0.26 | 0.079% |
| Natural Orange Flavor Emulsion | Edlong Corporation | 460 | 0.21 | 0.064% |
| Sodium Benzoate Powder, F.C.C. | Spectrum Chemical | S1146 | 0.18 | 0.055% |
| Natural Juicy (Citrus) Accord | Robertet | NV-18, 216 | 0.13 | 0.040% |
| Ascorbic Acid Powder F.C.C. | Spectrum Chemical | A1371 | 0.08 | 0.024% |
| Potassium Sorbate Powder, F.C.C. | Spectrum Chemical | P1408 | 0.01 | 0.003% |
| | | | 328.86 | 100.00% |

YIELD: 100%

Procedure for making 11.6 oz. Tangerine Orange Joint Juice—w/10% Calcium, 100% Vitamin C, 1500 mg Glucosamine HCl:

1. Dissolve sodium benzoate and potassium sorbate in water.
2. Preblend all other dry ingredients.
3. Add preblend to water with sodium benzoate & potassium sorbate.
4. Stir until completely dissolved.
5. Add all remaining ingredients.
6. Mix together well.
7. Carbonate.

Specifications for 11.6 oz. Tangerine Orange Joint Juice—w/10% Calcium, 100% Vitamin C, 1500 mg Glucosamine HCl:

pH: 3.48

Brix: 10.40°

TA: 0.58

TABLE 14

11.6 oz. Tropical Joint Juice Beverage

| Ingredient | Supplier | Code | Weight (g) | Percent |
|---|---|---|---|---|
| Water | | | 284.77 | 86.596% |
| 55 HFCS | Cargill | 55% | 31.64 | 9.621% |
| Orange Juice Concentrate | Vita-Pakt | 185 | 5.62 | 1.709% |
| Citric Acid | ADM | fine granular | 1.86 | 0.566% |
| Glucosamine HCl | Biosynergy | | 1.79 | 0.544% |
| Mango Concentrate, Totapuri | I.T.I. | 28° Brix | 1.22 | 0.371% |
| Passionfruit Concentrate | Smucker's | 50° Brix | 0.53 | 0.161% |
| Calcium Hydroxide Powder | VWR Scientific | 1374-01 | 0.26 | 0.079% |
| Natural Mandarin Orange Flavor | Givaudan-Roure | 470603 | 0.26 | 0.079% |
| Natural Orange Flavor | Robertet | NV-6507 | 0.21 | 0.064% |
| Natural Juicy (Citrus) Accord | Robertet | NV-18, 216 | 0.21 | 0.064% |
| Sodium Benzoate Powder, F.C.C. | Spectrum Chemical | S1146 | 0.18 | 0.055% |
| Natural Red Color, liquid | Wild | FACX648 | 0.12 | 0.036% |
| Natural Mango Flavor | Givaudan Roure | 436960 | 0.09 | 0.027% |
| Ascorbic Acid Powder, F.C.C. | Spectrum Chemical | A1371 | 0.08 | 0.024% |
| Potassium Sorbate Powder, F.C.C. | Spectrum Chemical | P1408 | 0.01 | 0.003% |
| | | | 328.85 | 100.000% |

YIELD: 100%

Procedure for making 11.6 oz. Tropical Joint Juice Beverage:

1. Dissolve sodium benzoate and potassium sorbate in water.
2. Preblend all other dry ingredients.
3. Add preblend to water with sodium benzoate & potassium sorbate.
4. Stir until completely dissolved.
5. Add all remaining ingredients.
6. Mix together well.
7. Carbonate.

Specifications for 11.6 oz. Tropical Joint Juice Beverage:

pH: 3.34

Brix: 10.40°

TA: 0.66

TABLE 15

Sugar-Free 11.6 oz. Lemon Joint Juice (Lemon RTD Beverage)

| Ingredient | Supplier | Code | Weight (g) | Percent |
|---|---|---|---|---|
| Water | | | 321.24 | 97.683% |
| Lemon Juice Concentrate | Vita-Pakt | 244 | 3.43 | 1.043% |
| Glucosamine HCl | Biosynergy | | 1.79 | 0.544% |
| Natural Lemon Flavor, WONF | Givaudan Roure | 881937 | 0.95 | 0.289% |
| Citric Acid | ADM | fine granular | 0.60 | 0.182% |
| Calcium Hydroxide Powder | VWTR Scientific | 1374-01 | 0.26 | 0.079% |
| Sodium Benzoate Powder F.C.C. | Spectrum Chemical | S1146 | 0.18 | 0.055% |
| Natural Lemon Extract Flavor | Ungerer | FG8949 | 0.16 | 0.049% |
| Natural Juicy (Citrus) Accord | Robertet | NV-18, 216 | 0.13 | 0.040% |

TABLE 15-continued

Sugar-Free 11.6 oz. Lemon Joint Juice (Lemon RTD Beverage)

| Ingredient | Supplier | Code | Weight (g) | Percent |
|---|---|---|---|---|
| Ascorbic Acid Powder F.C.C. | Spectrum Chemical | A1371 | 0.08 | 0.024% |
| Aspartame | Nutrasweet | Granular 100 | 0.02 | 0.006% |
| Acesulfame K | Hoechst | Sunett | 0.01 | 0.003% |
| Potassium Sorbate Powder F.C.C. | Spectrum Chemical | P1408 | 0.01 | 0.003% |
| | | | 328.86 | 100.000% |

YIELD: 100%

Procedure for making Sugar-Free 11.6 oz. Lemon Joint Juice (Lemon RTD Beverage):
1. Dissolve sodium benzoate and potassium sorbate in 21.24 g water.
2. Preblend all other dry ingredients.
3. Add preblend to water with sodium benzoate & potassium sorbate.
4. Stir until completely dissolved.
5. Add all remaining ingredients.
6. Mix together well.
7. Add 300 g seltzer water.

Specifications for Sugar-Free 11.6 oz. Lemon Joint Juice (Lemon RTD Beverage):
pH: 3.40
Brix: 2.2°
TA: 0.516

TABLE 16

11.6 oz. Sugar-Free Orange-w/10% Calcium, 100% Vitamin C, 1500 mg Glucosamine HCl

| Ingredient | Supplier | Code | Weight (g) | Percent |
|---|---|---|---|---|
| Water | | | 315.70 | 96.001% |
| Orange Juice Concentrate | Vita-Pakt | 185 | 7.50 | 2.281% |
| Glucosamine HCl | Biosynergy | | 1.79 | 0.544% |
| Citric Acid | ADM | fine granular | 1.67 | 0.508% |
| Natural Mandarin Orange Flavor | Givaudan-Roure | 470603 | 0.84 | 0.255% |
| Calcium Hydroxide Powder | VWR Scientific | 1374-01 | 0.26 | 0.079% |
| Natural Orange Flavor | Robertet | NV-6507 | 0.35 | 0.106% |
| Natural Orange Flavor Emulsion | Edlong Corporation | 460 | 0.30 | 0.091% |
| Sodium Benzoate Powder F.C.C. | Spectrum Chemical | S1146 | 0.18 | 0.055% |
| Natural Juicy (Citrus) Accord | Robertet | NV-18, 216 | 0.13 | 0.040% |
| Ascorbic Acid Powder F.C.C. | Spectrum Chemical | A1371 | 0.08 | 0.024% |
| Aspartame | Nutrasweet | Granular 100 | 0.02 | 0.006% |
| Acesulfame K | Hoechst | Sunett | 0.02 | 0.006% |
| Potassium Sorbate Powder F.C.C. | Spectrum Chemical | P1408 | 0.01 | 0.003% |
| | | | 328.85 | 100.00% |

YIELD: 100%

Procedure for making: 11.6 oz. Sugar-Free Orange—w/10% Calcium, 100% Vitamin C, 1500 mg Glucosamine HCl:
1. Dissolve sodium benzoate and potassium sorbate in 15.70 g water.
2. Preblend all other dry ingredients.
3. Add preblend to water with sodium benzoate & potassium sorbate.
4. Stir until completely dissolved.
5. Add all remaining ingredients.
6. Mix together well.
7. Add 300 g seltzer water.

Specifications for 11.6 oz. Sugar-Free Orange—w/10% Calcium, 100% Vitamin C, 1500 mg Glucosamine HCl:
pH: 3.53
Brix: 3.2°
TA: 0.611

TABLE 17

11.6 oz. Sugar-Free Tropical Joint Juice Beverage

| Ingredient | Supplier | Code | Weight (g) | Percent |
|---|---|---|---|---|
| Water | | | 314.39 | 95.603% |
| Orange Juice Concentrate | Vita-Pakt | 185 | 7.00 | 2.129% |
| Citric Acid | ADM | fine granular | 1.86 | 0.566% |
| Glucosamine HCl | Biosynergy | | 1.79 | 0.544% |
| Mango Concentrate, Totapuri | I.T.I. | 28° Brix | 1.45 | 0.441% |
| Passionfruit Concentrate | Smucker's | 50° Brix | 0.60 | 0.182% |
| Calcium Hydroxide Powder | VWR Scientific | 1374-01 | 0.26 | 0.079% |
| Natural Mandarin Orange Flavor | Givaudan-Roure | 470603 | 0.35 | 0.106% |
| Natural Orange Flavor | Robertet | NV-6507 | 0.30 | 0.091% |
| Natural Juicy (Citrus) Accord | Robertet | NV-18, 216 | 0.30 | 0.091% |
| Sodium Benzoate Powder F.C.C. | Spectrum Chemical | S1146 | 0.18 | 0.055% |
| Natural Red Color, liquid | Wild | FACX648 | 0.12 | 0.036% |
| Natural Mango Flavor | Givaudan Roure | 436960 | 0.12 | 0.036% |
| Ascorbic Acid Powder F.C.C. | Spectrum Chemical | A1371 | 0.08 | 0.024% |
| Aspartame | Nutrasweet | Granular 100 | 0.02 | 0.006% |
| Acesulfame K | Hoechst | Sunett | 0.02 | 0.006% |
| Potassium Sorbate Powder F.C.C. | Spectrum Chemical | P1408 | 0.01 | 0.003% |
| | | | 328.85 | 100.000% |

YIELD: 100%

Procedure for making 11.6 oz. Sugar-Free Tropical Joint Juice Beverage:
1. Dissolve sodium benzoate and potassium sorbate in 14.39 g water.
2. Preblend all other dry ingredients.
3. Add preblend to water with sodium benzoate & potassium sorbate.
4. Stir until completely dissolved.
5. Add all remaining ingredients.
6. Mix together well.
7. Add 300 g seltzer water.

Specifications 11.6 oz. Sugar-Free Tropical Joint Juice Beverage:
pH: 3.40
Brix: 3.4°
TA: .0.708

EXAMPLES 18

Snack Bars with Cartilage Supplements

TABLE 18

Chocolate Joint Bar

| Ingredient | Supplier | Code | Weight (g) | Percent |
|---|---|---|---|---|
| Chocolate Joint Bar: | | | | |
| Cereal Dough | | | 41.00 | 68.3333% |
| Coating | | | 19.00 | 31.6667% |
| | | | 60.00 | 100.0000% |
| Cereal Dough: | | | | |
| Brown Rice Syrup | Calif. Nat | 70 DE | 92.00 | 22.3681% |
| Oats, quick cook | Quaker | | 60.00 | 14.5879% |
| Brown Sugar | | | 55.00 | 13.3722% |
| Nutty Rice | | | 50.00 | 12.1566% |
| Rice Crispies | | | 50.00 | 12.1566% |
| Fructose | Cargill | 55 DE | 45.00 | 10.9409% |
| Soy Nut Grits | | | 20.00 | 4.8626% |
| Peanut Flour | | | 15.00 | 3.6470% |
| Glucosamine HCl | | | 9.00 | 2.1882% |
| Modified Food Starch, ultratex 4 | | | 6.80 | 1.6533% |
| Vanilla Flavor Extract | Nielson Massey | 2X | 3.00 | 0.7294% |
| Chocolate Flavor | Gividan | | 3.00 | 0.7294% |
| Avicel | | CL-611F | 2.50 | 0.6078% |
| Yield: | | | 411.30 | 100.0000% |

Procedure for making Chocolate Joint Bar:
1. Pre-blend wet ingredients.
2. Pre-blend dry ingredients and fold into wet.
3. Press 55 grams into mini loaf pans.
4. Bake

TABLE 19

Chocolate Joint Bar

| Ingredients | Supplier | Code | Weight (g) | Percent |
|---|---|---|---|---|
| Components: | | | | |
| Kaorich Beads | | | 8.10 | 2.01% |
| Kaomel Flakes | | | 60.30 | 14.99% |
| Chocolate Compound | | | 334.00 | 83.00% |
| Coating | | | | |
| | | | 402.40 | 83.00% |

TABLE 20

Chocolate Joint Bar

| Ingredient | Supplier | Code | Weight (g) | Percent |
|---|---|---|---|---|
| Chocolate Joint Bar: | | | | |
| Cereal Dough | | | 41.00 | 68.3333% |
| Coating | | | 19.00 | 31.6667% |
| | | | 60.00 | 100.0000% |
| Cereal Dough: | | | | |
| Brown Rice Syrup | Calif. Nat | 70 DE | 92.00 | 22.0175% |
| Oats, quick cook | Quaker | | 60.00 | 14.3592% |
| Brown Sugar | | | 55.00 | 13.1626% |
| Nutty Rice | | | 50.00 | 11.9660% |
| Rice Crispies | | | 50.00 | 11.9660% |
| Fructose | Cargill | 55 DE | 45.00 | 10.7694% |
| Soy Nut Grits | | | 20.00 | 4.7864% |
| Peanut Flour | | | 15.00 | 3.5898% |
| Glucosamine HCl | | | 9.00 | 2.1539% |
| Chondroitin Sulfate | | | 7.50 | 1.7949% |
| Modified Food Starch, ultratex 4 | | | 6.00 | 1.4359% |
| Vanilla Flavor Extract | Nielson Massey | 2X | 3.00 | 0.7180% |
| Chocolate Flavor | Gividan | | 3.00 | 0.7180% |
| Avicel | | CL-611F | 2.30 | 0.5504% |
| Manganese Sulfate | | | 0.05 | 0.0120% |
| Yield: | | | 417.85 | 100.0000% |

Procedure for making Chocolate Joint Bar:
1. Pre-blend wet ingredients.
2. Pre-blend dry ingredients and fold into wet.
3. Press 55 grams into mini loaf pans.
4. Bake

TABLE 21

Chocolate Joint Bar

| Ingredient | Supplier | Code | Weight (g) | Percent |
|---|---|---|---|---|
| Components: | | | | |
| Kaorich Beads | | | 8.10 | 2.01% |
| Kaomel Flakes | | | 60.30 | 14.99% |
| Chocolate Compound | | | 334.00 | 83.00% |
| Coating | | | | |
| | | | 402.40 | 83.00% |

TABLE 22

Stone Clinic Bar/Calif. type
Contributions based on bar size of 60 grams

| Ingredient | Supplier | Code | Weight (g) | BAR (g) | Percent |
|---|---|---|---|---|---|
| Granola Matrix: | | | | | |
| Rolled Oats | Quaker | Quick Oats | 55.00 | 18.53 | 30.89% |
| Apples, dried | Sunsweet | | 22.42 | 7.55 | 12.59% |
| Water | | | 20.00 | 6.74 | 11.23% |
| Honey | SueBee | | 20.00 | 6.74 | 11.23% |
| Dark Brown Sugar | C&H | | 20.00 | 6.74 | 11.23% |
| Modified Food Starch | National | Purity Gum | 14.14 | 4.76 | 7.94% |
| Crisp Rice | Kellogg | | 7.50 | 2.53 | 4.21% |
| Soybean Oil | Wesson | | 5.00 | 1.69 | 2.81% |
| Glucosamine HCl | Optimal Nutrients | | 4.45 | 1.50 | 2.50% |
| Chondroitin Sulfate | Optimal Nutrients | | 3.58 | 1.21 | 2.01% |
| Wheat Germ | Quaker | | 3.50 | 1.18 | 1.97% |
| Apple Flavor | Robertet | NV 50078 | 0.42 | 0.14 | 0.24% |

TABLE 22-continued

Stone Clinic Bar/Calif. type
Contributions based on bar size of 60 grams

| Ingredient | Supplier | Code | Weight (g) | BAR (g) | Percent |
|---|---|---|---|---|---|
| Vanilla Extract | Nielsen Massey | 4X | 0.80 | 0.27 | 0.45% |
| Salt | Morton | Culinox 999 | 0.62 | 0.21 | 0.35% |
| Cinnamon, ground | McCormick | | 0.58 | 0.20 | 0.33% |
| Manganese Sulfate | Fortitech | | 0.015 | 0.006 | 0.01% |
| Yield: | | | 178.03 | 60.00 | 100.00% |

Procedure for making Stone Clinic Bar/Calif. type:
1. Combine honey, vegetable oil, vanilla extract and starch; mix well.
2. Preblend the rest of the ingredients.
3. Using Kitchen Aid with paddle attachment, add dry ingredients to bowl
4. Slowly add starch slurry while mixing on slow speed.
5. Mix until a cookie dough consistency (3 minutes) on speed 1.
6. Spray a light coating of Pam in small bread pan.
7. Press down firmly.
8. Pre-heat convection oven to 300° F.; bake for 13-15 minutes
9. Cool and cut into bars weighing 60 grams each.

TABLE 23

Orange Chew B: 550 mg Glucosamine HCl, 60 mg Vit C,
100 mg Calcium Changed ratio of corn syrups

| Ingredient | Supplier | Code | Weight (g) | Percent |
|---|---|---|---|---|
| Sugar, granulated | C & H | | 200.00 | 44.18% |
| 63 DE Corn Syrup | Cargill | | 36.88 | 8.15% |
| 36 DE Corn Syrup | Cargill | | 110.62 | 24.44% |
| Water | | | 20.00 | 4.42% |
| Glucosamine HCl | | | 35.50 | 7.84% |
| Calcium Carbonate | | | 18.00 | 3.98% |
| Partially Hydrogenated Vegetable Oil | Loders Croklaan | Kaomel | 18.00 | 3.98% |
| Vitamin C | Spectrum | A1371 | 4.00 | 0.88% |
| Modified Food Starch | National | Pure-Gel 990 | 4.00 | 0.88% |
| Citric Acid | ADM | fine granular | 2.00 | 0.44% |
| Orange Flavor | Robertet | NV-6507 | 1.00 | 0.22% |
| Tangerine Flavor | Givaudan Roure | | 0.50 | 0.11% |
| Lecithin | Central Soya | Centrolex F | 1.00 | 0.22% |
| Orange Color Liquid | Warner-Jenkinson | 404 | 0.40 | 0.09% |
| Natural Juicy Flavor Accord | Robertet | | 0.75 | 0.17% |
| YIELD: 100% | | | 452.65 | 100.00% |

Procedure for making Orange Chew B:
1. Preblend sugar, calcium and citric acid.
2. Add preblend to corn syrups in a saucepan.
2. Heat sugar solution to 285° F. Remove from heat.
3. Stir in vegetable oil and lecithin. Set aside.
4. In a separate container, dissolve glucosamine in water (20 g).
5. Blend in Vitamin C, citric acid and calcium carbonate.
6. Stir in orange color and flavors. Set aside.
7. Whisk orange mixture into sugar/oil solution.
8. Pour mixture into a Kitchen Aid mixer bowl.
9. Using wire whisk attachment, mix on HIGH for 2 minutes.
10. Allow mixture to cool to 85° F.
11. Form into 7 gram cubes.
12. Wrap individually with wax paper.

TABLE 24

Orange Juice Bars
Version C

| Ingredients | Supplier | Code | Weight (g) | Percent |
|---|---|---|---|---|
| Water | | filtered | 40.00 | 18.22% |
| Corn Syrup | Staley | Hi Fructose | 40.00 | 18.22% |
| Protein Blend | | | 30.00 | 13.66% |
| Yogurt Compound | Guittard | | 30.00 | 13.66% |
| Crisp Rice | Kelloggs | | 20.00 | 9.11% |
| Sugar | C & H | granular | 20.00 | 9.11% |
| Purity Gum | National | | 28.28 | 12.88% |
| Orange Powder | Crystals Inter. | | 5.00 | 2.28% |
| Part. Hydrogen. Oil | Loders Croklaan | 321 | 5.00 | 2.28% |
| Orange Flavor | | | 1.28 | 0.58% |
| Tumeric | | | 0.01 | 0.005% |
| | | | 219.57 | 100.00% |

Procedure for making Orange Juice Bars Version C
1. Blend water, corn syrup, purity gum and orange flavor; mix to make a slurry.
2. Preblend remaining dry ingredients.
3. In double boiler, melt yogurt compound with oil; stir until smooth.
4. In Hobart mixer, combine melted yogurt mixture with sugar; beat until creamy.
5. Stir dry mixture into sugar mixture. The mix will be dry.
6. Slowly add the slurry while mixing; beat on medium-high speed for 3 minutes.
7. Weight 100 grams of mix into bar greased bar molds; press down firmly.
8. Bake in convection oven at 300 F for 15 minutes.
9. Cool; trim to 60 grams; coat with yogurt compound coating.

Those of skill in the art will recognize that the invention may be embodied in other specific forms without departing from the spirit of essential characteristics thereof. The presently described embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. A beverage comprising a mixture of a juice drink base and a cartilage supplement-containing solution, wherein:
   (A) said juice drink base is a solution of water, ascorbic acid, potassium sorbate and naturally or artificially flavored fruit juice, prepared using a heat pasteurization process at a temperature above 190° F.,
   (B) said cartilage supplement-containing solution is a water-based solution comprising one or more cartilage supplements and prepared at a temperature of 150° F. or below, whereby inactivation of the cartilage supplement is substantially minimized,
   (C) said one or more cartilage supplements are selected from the group consisting of glucosamine, glucosamine salts, glucosamine associated with a counterion, glucosamine derivatives that dissociate to glucosamine in water or after ingestion, chondroitin, chondroitin salts, chondroitin associated with a counterion, and hyaluronic acid, (D) said mixture is obtained by cooling the juice drink base to a temperature of 150° F. or less and adding and mixing the cartilage supplement-containing solution and a sweetener, wherein the sweetener is stevia, and (E) the pH of the beverage is in the range of 2.2 to 4.6.

2. The beverage according to claim 1 wherein said cartilage supplement is glucosamine.

3. The beverage according to claim 1 wherein said cartilage supplement is chondroitin.

4. The beverage according to claim 1 wherein the cartilage supplement is selected from the group consisting of glucosamine salts, glucosamine associated with a counterion, glucosamine derivatives that dissociate to glucosamine in water or after ingestion, chondroitin salts, and chondroitin associated with a counterion.

5. The beverage according to claim 1 wherein the cartilage supplement is glucosamine hydrochloride.

6. The beverage according to claim 1 wherein said naturally or artificially flavored fruit juice is fruit juice.

7. The beverage according to claim 1 wherein said naturally or artificially flavored fruit juice is fruit juice concentrate.

8. The beverage according to claim 1 wherein said mixture is carbonated.

9. The beverage according to claim 1 wherein said mixture is not carbonated.

10. The beverage according to claim 1 wherein the step of adding and mixing the cartilage supplement-containing solution with the cooled juice drink base is carried out at a temperature of 35° F. to 150° F.

11. The beverage of claim 1 wherein the cartilage supplement is glucosamine hydrochloride.

12. A method for preparing a beverage, comprising the steps of:

(A) providing a juice drink base, said juice drink base being a solution of water, ascorbic acid, potassium sorbate and naturally or artificially flavored fruit juice, prepared using a heat pasteurization process at a temperature above 190° F, (B) providing a cartilage supplement-containing solution, which is a water-based solution comprising one or more cartilage supplements and prepared at a temperature of 150° F. or below, whereby inactivation of the cartilage supplement is substantially minimized, and wherein said one or more cartilage supplements are selected from the group consisting of glucosamine, glucosamine salts, glucosamine associated with a counterion, glucosamine derivatives that dissociate to glucosamine in water or after ingestion, chondroitin, chondroitin salts, chondroitin associated with a counterion, and hyaluronic acid, (C) forming a mixture by cooling the juice drink base to a temperature of 150° F. or less, and adding and mixing the cartilage supplement-containing solution and a sweetener, wherein the sweetener is stevia, and (E) adjusting the pH of the mixture in the range of 2.2 to 4.6 to obtain the beverage.

13. The method according to claim 12 wherein said cartilage supplement is glucosamine.

14. The method according to claim 12 wherein said cartilage supplement is selected from the group consisting of glucosamine, glucosamine salts, glucosamine associated with a counterion and glucosamine derivatives that dissociate to glucosamine in water or after ingestion.

15. The method according to claim 12 wherein said cartilage supplement is glucosamine hydrochloride.

16. The method according to claim 12 comprising the further step of carbonating said mixture.

17. A method of treating cartilage dysfunction comprising:

(i) preparing a cartilage enhancing beverage, said beverage containing a mixture of a juice drink base and a cartilage supplement-containing solution, wherein:

(A) said juice drink base is a solution of water, ascorbic acid, potassium sorbate and naturally or artificially flavored fruit juice, prepared using a heat pasteurization process at a temperature above 190° F., (B) said cartilage supplement-containing solution is a water-based solution comprising one or more cartilage supplements and prepared at a temperature of 150° F. or below, whereby inactivation of the cartilage supplement is substantially minimized, (C) said one or more cartilage supplements are selected from the group consisting of glucosamine, glucosamine salts, glucosamine associated with a counterion, glucosamine derivatives that dissociate to glucosamine in water or after ingestion, chondroitin, chondroitin salts, chondroitin associated with a counterion, and hyaluronic acid, (D) said mixture is obtained by cooling the juice drink base to a temperature of 150° F. or less and adding and mixing the cartilage supplement-containing solution and a sweetener, wherein the sweetener is stevia, and (E) the pH of the beverage is in the range of 2.2 to 4.6; and (ii) administering an effective amount of the cartilage enhancing beverage to a human in need of treatment for cartilage dysfunction.

18. The method according to claim 17 wherein said cartilage supplement is glucosamine hydrochloride.

19. The method of claim 17 wherein the juice drink base contains flavored water, fruit juice concentrate, fruit juice, fruit flavored juice, or combinations thereof.

20. The method according to claim 17 wherein the beverage is carbonated.

* * * * *